United States Patent [19]

Fujii et al.

[11] Patent Number: 4,757,138

[45] Date of Patent: Jul. 12, 1988

[54] PROCESS FOR PRODUCING ETOPOSIDE

[75] Inventors: Tadashi Fujii, Iwatsuki; Yukio Chikui, Tokyo, both of Japan

[73] Assignee: Nippon Kayaku Kabushiki Kaisha, Tokyo, Japan

[21] Appl. No.: 904,372

[22] Filed: Sep. 8, 1986

Related U.S. Application Data

[63] Continuation of Ser. No. 733,918, May 14, 1985.

[30] Foreign Application Priority Data

May 22, 1984 [JP] Japan ................................. 59-101766

[51] Int. Cl.$^4$ ........................................... C07H 15/24
[52] U.S. Cl. .................................. 536/18.1; 536/4.1; 536/115; 536/120
[58] Field of Search ........................ 536/4.1, 18.1, 120, 536/115

[56] References Cited

U.S. PATENT DOCUMENTS 4,564,675 1/1986 Kurabayashi et al. .............. 536/18.1

OTHER PUBLICATIONS

Chemical Abstracts, vol. 101, No. 3, Jul. 1984, p. 639, No. 23883h, Columbus, Ohio.
Chemical Abstracts, vol. 100, No. 21, May 1984, p. 670, No. 175210d, Columbus, Ohio.
EP-A-O 111 058 (Nippon Kayaku K.K.), p. 7, III-I, pp. 18, 20, claim 10.
Protective Groups in Organic Synthesis (T. W. Greene) (1982), pp. 55 and 56.

Primary Examiner—J. R. Brown
Assistant Examiner—Elli Peselev
Attorney, Agent, or Firm—Cushman, Darby & Cushman

[57] ABSTRACT

The present invention relates to a process for producing etoposide by reacting a 4′-halogenoacetyl-4′-demethylepipodophyllotoxin-$\beta$-D-2,3-di-O-halogenoacetyl-4,6-O-ethylideneglucoside represented by the general formula:

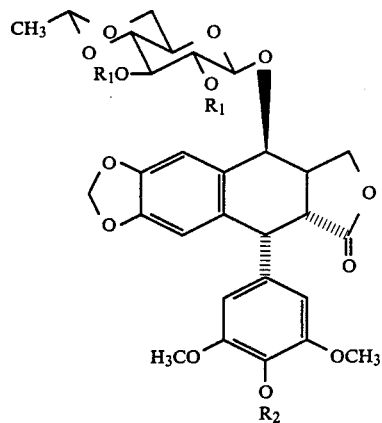

wherein $R_1$ and $R_2$, which may be the same or different, represent each —COCHX$_2$ or —COCX$_3$, wherein X represents a halogen atom, with an alcohol, an amine, and/or ammonia to remove the halogenoacetyl groups.

6 Claims, No Drawings

PROCESS FOR PRODUCING ETOPOSIDE

This is a continuation of application Ser. No. 733,198 filed May 14, 1985.

BACKGROUND OF THE INVENTION

A process for producing etoposide represented by the formula:

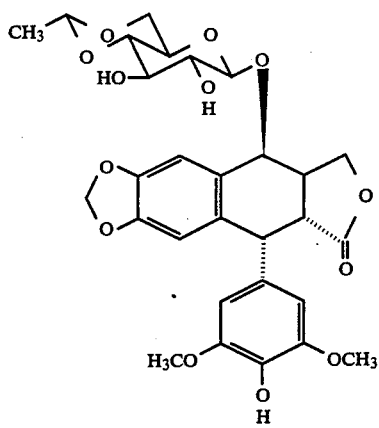

(I)

comprising the following steps (1) and (2) is already known (see Canadian Pat. No. 956939):

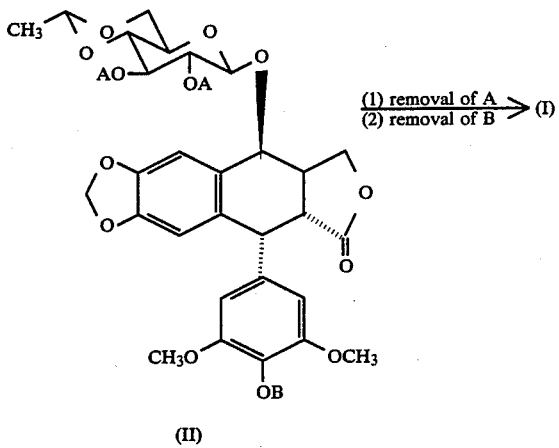

wherein A represents formyl or acetyl, and B represents benzyloxycarbonyl.

However, the above process has drawbacks that two steps, i.e., a step of removing A and a subsequent step of removing B, are necessary, the removal of A is time-consuming (for example, the reaction can not be completed even after 20 to 30 hours) and, because of the increased production of by-products such as colored products, the quality of the produced etoposide is poor and its yield is low.

DETAILED DESCRIPTION OF THE INVENTION

As a result of a variety of studies about a novel process for producing etoposide, the inventors of the present invention have found that by using a compound represented by formula (III):

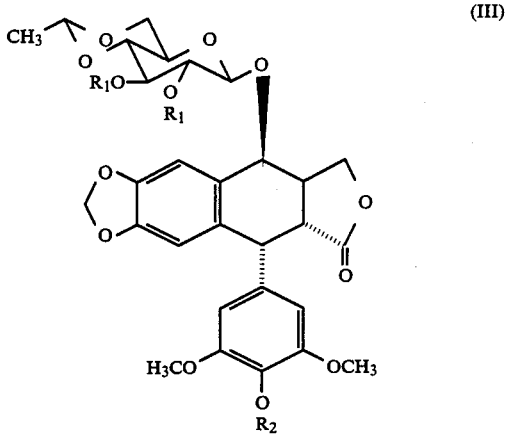

(III)

wherein $R_1$ and $R_2$, which may be the same or different, represent each $-COCHX_2$ or $-COCX_3$, wherein X represents a halogen atom, obtained by utilizing a di- or tri-halogenoacetyl halide as a starting material, and reacting this compound with an alcohol, an amine and-/or ammonia, $R_1$ and $R_2$ can be removed simultaneously to obtain etoposide and that the obtained etoposide is low in an impurity content so that it can be easily purified.

The present invention has been completed on the basis of the above finding.

The present invention will now be described in more detail. As examples of X in $R_1$ and $R_2$ of a compound of formula (III) used as a starting material in the present invention, fluorine, chlorine, bromine, and iodine can be mentioned, among which chlorine or bromine is particularly desirable. As examples of $R_1$ and $R_2$, difluoroacetyl, dichloroacetyl, dibromoacetyl, diiodoacetyl, trifluoroacetyl, trichloroacetyl, tribromoacetyl, and triiodoacetyl can be mentioned.

As examples of the alcohols which can be used in this invention, there can be mentioned lower ($C_1$–$C_4$) alcohols having 1 to 3 hydroxyl groups and lower amino alcohols having 1 to 3 lower hydroxyalkyl groups on the nitrogen atom, and more particularly, lower monohydric alcohols such as methanol, ethanol, propanol, and butanol; lower polyhydric alcohols such as ethylene glycol and glycerine; and lower ($C_1$–$C_4$) amino alcohols such as monoethanolamine, dimethanolamine, and tripropanolamine, among which lower monohydric alcohols such as methanol and ethanol are desirable. It is desirable to use these alcohols as solvents for the present reaction, but alcohols other than these may be used. In this case, it is suitable that the alcohol is used usually in an amount at least equivalent to that of compound (III).

As the amines which can be used in the present invention, there can be mentioned $C_1$–$C_6$ aliphatic primary amines such as methylamine, ethylamine, n-propylamine, and n-butylamine; $C_1$–$C_6$ aliphatic secondary amines such as dimethylamine, diethylamine, di-n-propylamine, di-n-butylamine, and di-n-hexylamine; $C_4$–$C_5$ cyclic amines which may contain oxygen atoms, such as pyrrolidine, piperidine, and morpholine, and aliphatic diamines such as ethylenediamine, among which the lower alkyl primary and secondary amines such as methylamine and diethylamine are desirable. When these amines and/or ammonia are used, these may be used as solvents, but is is usually desirable to use some other solvents.

In this case, its amount is usually at least equivalent or preferably 1 to 3 equivalents per equivalent of compound (III). Although it is of course possible to add an amine or ammonia as such to the reaction system, it is also possible that an acetate or hydrochloride of an amine and/or ammonia is added in the presence of a base, for example, pyridine or triethylamine to the reaction system and to effect the reaction with the free amine and/or ammonia prepared in situ.

In the present invention, said alcohols, amines, or ammonia may be used alone or as a mixture of at least two of them. When they are used in the form of a mixture, it is desirable that an alcohol is used as the solvent. In this case, it is suitable that an amine or ammonia is used in an amount of about 1 to 10 equivalents, preferably about 1 to 3 equivalents per equivalent of compound (III).

The use of compounds other than the alcohols, amines, an ammonia as the solvent is not particularly limited so far as they do not adversely affect the reaction and, as examples of these compounds, chloroform, ether, 1,2-dichloroethylene, dimethylformamide, and pyridine can be mentioned.

The reaction of the present invention, especially the reaction with an alcohol can proceed smoothly when a lower tertiary alkylamine such as trimethylamine or triethylamine, a pyridine such as pyridine or a loweralkyl-substituted pyridine, or an organic carboxylic acid salt is added as a catalyst to the reaction system. As the organic carboxylic acid salts, there can be mentioned (1) metal salts or ammonium salts of an at least monobasic aliphatic carboxylic acids, for example, sodium acetate, potassium acetate, magnesium acetate, sodium propionate, sodium succinate, ammonium formate, ammonium acetate, ammonium malonate, ammonium succinate, and alkylammonium acetate, (2) metal salts (alkali metal salts or alkaline earth metal salts) or ammonium salts of aromatic carboxylic acids, for example, sodium benzoate, ammonium isonicotinate, ammonium benzoate, ammonium anthranilate, and alkylammonium benzoate, and (3) ammonium salt- or metal salt-form (alkali metal salt-form or alkaline earth metal salt-form) weakly acidic cation exchange resins having carboxyl groups as exchangeable groups. Among them ammonium salts, desirably $C_1$–$C_3$ saturated fatty acid ammonium salts, more desirably, ammonium acetate and ammonium formate are preferred, and the amount of these compounds are about 5–100 w/w %, more desirably about 30–50 w/w %, based on the compound of the general formula (III).

The temperature in the present invention varies with a solvent or catalyst used, but it is usually −10° to 100° C., desirably 0° to 90° C., especially 20° to 70° C., and the reaction is brought to completion within about 0.1 to 7 hours.

The compound of formula (III) which is used as a starting material in the present invention is a novel substance not described in literature, and it can be synthesized by using well-known 4′-demethylepipodophyllotoxin (IV) (see U.S. Pat. No. 3524844) as a starting material, and reacting this through, for example, the following reaction routes:

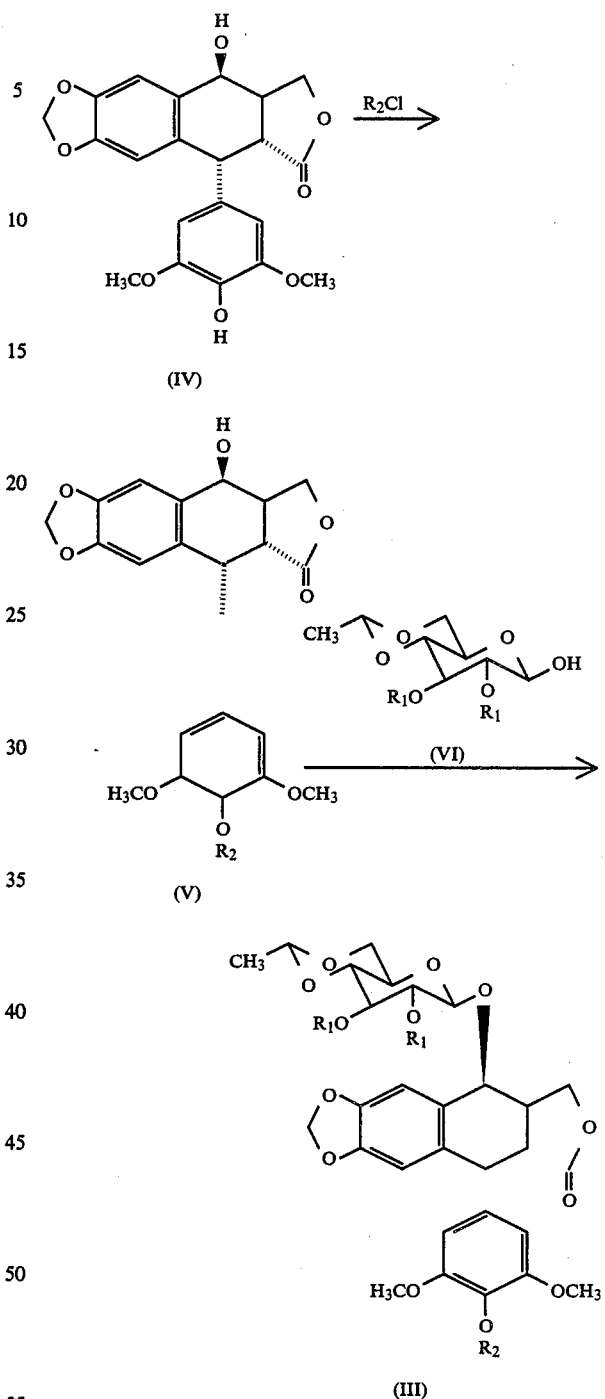

wherein $R_1$ and $R_2$ are as defined above. Namely, the compound (I) can be obtained by reacting 4′-demethylepipodophyllotoxin (IV) with a dihalogeno- or trihalogeno-acetyl chloride ($R_2Cl$) in an inert solvent and condensing the resulting 4′-halogenoacetyl-4′-demethylepipodophyllotoxin (V) with a 4,6-O-ethylidene-2,3-di-O-halogenoacetyl-β-D-glycopyranose (VI) at a temperature lower than 0° C. in an inert solvent in the presence of boron trifluoride ethyl etherate. It is suitable that the glucopyranose of the general formula (IV) is used in an amount of at least one equivalent per equivalent of the compound of the general formula (V).

Here, the compound (VI) is a novel one, and can be synthesized by using a well-known 4,6-O-ethylidene-1-O-benzyloxycarbonyl-β-D-glucopyranose (VII) as a starting material through, for example, the following reaction routes:

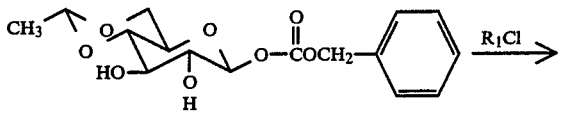

(VII)

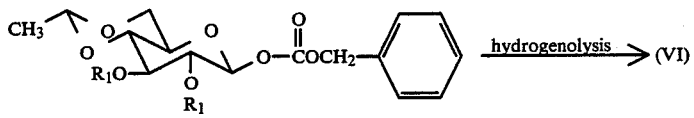

(VIII)

wherein $R_1$ is as defined above. Namely, the compound (VI) can be obtained by reacting 4,6-O-ethylidene-1-O-benzyloxycarbonyl-β-D-glucopyranose (VII) with dihalogeno- or trihalogeno-acetyl chloride in an inert solvent and subjecting the resulting 4,6-O-ethylidene-1-O-benzyloxycarbonyl-2,3-di-O-halogeno-acetyl-β-D-glucopyranose (VIII) to hydrogenolysis. Here, although the formation of a small amount of an α-isomer is not avoidable in the hydrogenolysis, the compound (VI) has such a property that the separation of an α-isomer from a β-isomer is easy because only the β-isomer is crystallized selectively from the reaction solution. Further, the β-isomer of the compound (VI) has good stability, and undergoes substantially no isomerization into the α-isomer, so that it can be stored for a long time.

According to the present invention, the removal of the halogenoacetyl groups can be effected under a gentle condition, for example, at 25° C. or room temperature, within a short time, so that the formation of by-products such as colored products is little and it is possible to obtain etoposide from compound (III) in high yields. Therefore, purification after the reaction such as removal of colored products is easy and, for example, pure etoposide can be obtained by adding a hydrophobic solvent such as chloroform to the reaction solution, washing the solution with water, distilling off the solvent and recrytallizing the residue from a solvent. The resulting etoposide has such an extremely low inorganic content that its ignition residue (a residue left after ignition of etoposide) is 0.1% by weight or below. Further, when an alcohol is reacted in the presence of an ammonium salt of a lower fatty acid, such as ammonium acetate, or a tertiary amine, or when an alcohol is used in combination with an amine or ammonia in the present invention, the reaction is brought to completion within a short time at room temperature, and etoposide can be recovered merely by concentrating the reaction solution, so that the reaction operation and the after-treatment subsequent to the reaction are easy, and the process is extremely advantageous as an industrial production process. Particularly, in the latter case, the reaction can be brought to completion within a short time.

The present invention will now be described in detail with reference to examples.

EXAMPLE 1

1 g of 4'-dichloroacetyl-4'-demethylepipodophyllotoxin-β-D-2,3-di-O-dichloroacetyl-4,6-O-ethylideneglucoside (III) ($R_1$, $R_2$=—COCHCl$_2$) and 1 g of ammonium acetate were dissolved in 20 ml of methanol, and the solution was stirred at 25° C. for 1.5 hours. After completion of the reaction, the methanol was concentrated to 10 ml and the resulting solution was cooled to obtain 0.55 g (yield: 86.1%) of etoposide.

The $R_f$ value of TLC (silica gel, developer, chloroform:methanol (1:1)), IR, NMR, and optical rotation of the obtained crystal were identical to those of the substance obtained by the process of Canadian Pat. No. 956939.

m.p. 259°–260° C., $R_f$=0.44.

EXAMPLES 2 TO 9

1 g of compound (III) ($R_1$, $R_2$=—COCHCl$_2$) was reacted under conditions shown in the following table, and the reaction solution was treated in the same manner as in Example 1 to obtain etoposide.

| Example | Catalyst | Amount of methanol | Reaction temperature | Reaction time | Yield of etoposide (I) |
|---|---|---|---|---|---|
| 2 | HCO$_2$NH$_4$ | 1 g  20 ml | 25° C. | 3 hr | 86.5% |
| 3 | H$_2$CCO$_2$NH$_4$ \| H$_2$CCO$_2$NH$_4$ | 1 g  20 ml | 25° C. | 7 hr | 77.8% |
| 4 | ⌬—CO$_2$NH$_4$ | 1 g  20 ml | 25° C. | 4 hr | 82.4% |

| Example | Catalyst | Amount of methanol | Reaction temperature | Reaction time | Yield of etoposide (I) |
|---|---|---|---|---|---|
| 5 | 2-aminobenzoic acid ammonium salt (phenyl ring with NH$_2$ and CO$_2$NH$_4$) | 1 g | 20 ml | 25° C. | 4 hr | 81.5% |
| 6 | pyridine-2-carboxylic acid ammonium salt (N-containing ring with CO$_2$NH$_4$) | 1 g | 20 ml | 25° C. | 4 hr | 81.8% |
| 7 | 1-naphthoic acid ammonium salt (naphthalene with CO$_2$NH$_4$) | 1 g | 20 ml | 25° C. | 2 hr | 83.1% |
| 8 | 1-naphthylacetic acid ammonium salt (naphthalene with CH$_2$CO$_2$NH$_4$) | 1 g | 20 ml | 25° C. | 2 hr | 80.2% |
| 9 | weakly acidic ion exchange resin* | 1 g | 20 ml | 25° C. | 5 hr | 78.6% |

*WK-20 ® (N$^+$H$_4$): a product of Mitsubishi Chemical Industries, Ltd.

EXAMPLE 10

1 g of 4'-dichloroacetyl-4'-demethylepipodophyllotoxin-β-D-2,3-di-O-dichloroacetyl-4,6-O-ethylideneglucoside (III) ($R_1$, $R_2$=—COCHCl$_2$) and 1 g of magnesium acetate were refluxed for 4 hours in 20 ml of methanol. After completion of the reaction, the methanol was distilled off and, after adding 30 ml of chloroform, the residue was washed with water and dried over anhydrous magnesium sulfate. The solvent was distilled off in vacuum, and the residue was recrystallized from methanol to obtain 0.49 g (yield: 76.7%) of etoposide crystals.

EXAMPLE 11

4.75 g (yield: 64.6%) of etoposide crystals were obtained by the same reaction as in Example 1 except that compound (III) ($R_1$, $R_2$=—COCHCl$_2$) used in Example 1 was replaced with 4'-dibromoacetyl-4'-demethylepipodophyllotoxin-β-D-2,3-di-O-dibromoacetyl-4,6-O-ethylideneglucoside (III) ($R_1$, $R_2$=—COCHBr$_2$).

EXAMPLE 12

1 g of compound (III) ($R_1$, $R_2$=—COCHCl$_2$) was dissolved in 20 ml of methanol and after adding 0.64 g of diethylamine, the solution was stirred at 25° C. for 10 minutes. After completion of the reaction, the solvent was distilled off in vacuum. After adding 20 ml of chloroform, the residue was neutralized with 2N hydrochloric acid, washed with water, and dried over anhydrous magnesium sulfate. The solution was concentrated in vacuum to a volume of 10 ml to obtain 0.53 g (yield: 83.1%) of etoposide crystals.

EXAMPLE 13

0.51 g (yield: 80.0%) of etoposide crystals were obtained by the same reaction as in Example 12 except that diethylamine used in Example 12 was replaced with 0.88 g of di-n-propylamine.

EXAMPLE 14

1 g of compound (III) ($R_1$, $R_2$=—COCHCl$_2$) was added to 20 ml of methanol in which 0.15 g of ammonia gas had been dissolved, and the mixture was stirred at 25° C. for 30 minutes. After completion of the reaction, the solvent was distilled off in vacuum. After adding 10 ml of chloroform, the residue was recrystallized to obtain 0.54 g (yield: 84.7%) of etoposide crystals.

EXAMPLE 15

0.40 g (yield: 62.7%) of etoposide crystals were obtained by the same reaction as in Example 12 except that methanol used in Example 12 was replaced with 20 ml of diethylamine.

Likewise, the reaction was effected by replacing methanol used in Example 12 with 20 ml of pyridine.

EXAMPLE 16

Production of 4'-dichloroacetyl-4'-demethylepipodophyllotoxin-β-D-2,3-di-O-dichloroacetyl-4,6-O-ethylideneglycoside (III) ($R_1$, $R_2$=—COCHCl$_2$)

(a)-4'-dichloroacetyl-4'-demethylepipodophyllotoxin (V) ($R_2$=—COCHCl$_2$)

8 g of 4'-demethylepipodophyllotoxin (IV) was dissolved in 160 ml of acetone and, after 3.2 g of pyridine, the solution was cooled to −5° to −10° C. To this solution, 4.1 g of dichloroacetyl chloride was added dropwise over a period of 1.5 hours, and the solution was further stirred for 0.5 hour. The acetone was distilled off in vacuum, and the obtained solid was dissolved in 160 ml of 1,2-dichloroethane and washed with water. The 1,2-dichloroethane solution was dried over anhydrous magnesium sulfate, and then concentrated in vacuum to obtain 9.5 g (yield: 93.4%) of compound (V) $R_2$=—COCHCl$_2$).

m.p. 207°–208° C.

IR $\nu_{max}^{KBr}$ 3540, 1775, 1600, 1485, 1235, 1130 cm$^{-1}$.

(b) 4,6-O-ethylidene-1-O-benzyloxycarbonyl-2,3-di-O-dichloroacetyl-β-D-glucopyranose (VIII) ($R_1$=—COCHCl$_2$)

34.0 g of 4,6-O-ethylidene-1-O-benzyloxycarbonyl-β-D-glucopyranose (VII) was suspended in 340 ml of 1,2-dichloroethane and, after adding 23.7 g of pyridine, the suspension was cooled to 0° to 5° C. To this suspension, 32.4 g of dichloroacetyl chloride was added dropwise over a period of about one hour and further stirred for 0.5 hour. The reaction solution was washed with water, and the organic layer was dried over anhydrous magnesium sulfate and concentrated in vacuum to obtain 51.0 l g (yield: 90%) of compound (VIII) ($R_1$=—COCHCl$_2$).

m.p. 150°–151° C.

IR $\nu_{max}^{KBr}$ 1770, 1255, 1100, 820 cm$^{-1}$.

(c) 4,6-O-ethylidene-2,3-di-O-dichloroacetyl-β-D-glucopyranose (VI) ($R_1$=—COCHCl$_2$)

10.0 g of compound (VIII) ($R_1$=—COCHCl$_2$) was dissolved in 50 ml of acetone and, after adding 1.0 g of palladium black, the solution was subjected to hydrogenolysis at $-5°$ to $-10°$ C. and an elevated pressure. After completion of the reaction, the catalyst was filtered off, and the solvent was distilled off in vacuum. 17 ml of diisopropyl ether was added to the residue, and the mixture was cooled to 0° C. and filtered by suction to obtain 7.3 g (yield: 95.9%) of compound (VI) ($R_1$=—COCHCl$_2$).

m.p. 133°–135° C.

IR $\nu_{max}^{KBr}$ 3445, 1775, 1305, 1165, 1095, 1005, 815 cm$^{-1}$.

(d) 4'-dichloroacetyl-4'-demethylepipodophyllotoxin-β-D-2,3-di-O-dichloroacetyl-4,6-O-ethylideneglucoside (III) ($R_1$, $R_2$=—COCHCl$_2$)

3.0 g of compound (V) ($R_2$=—COCHCl$_2$) was dissolved in 60 ml of 1,2-dichloroethane and, after adding 2.5 g of compound (VI) ($R_1$=—COCHCl$_2$), the solution was cooled to $-10°$ C. 1.1 g of boron trifluoride ethyl etherate was added thereto dropwise over a period of about 1.5 hour, and, after completion of the addition, the reaction mixture was further stirred for 0.5 hour. 0.8 g of pyridine was added thereto dropwise while the internal temperature was being kept at $-5°$ to $-10°$ C., and the reaction mixture was washed with water. The organic layer was dried over anhydrous magnesium sulfate and concentrated in vacuum, and the residue was recrystallized from methanol to obtain 4.4 g (yield: 81.4%) of compound (III) ($R_1$, $R_2$=—COCHCl$_2$).

m.p. 207°–208° C.

IR $\nu_{max}^{KBr}$ 1880, 1610, 1490, 1240, 1130, 935, 820 cm$^{-1}$.

Further, compound (III) was obtained from 1.5 g of compound (V) and 5.0 g of compound (VI) by the same reaction and treatment as those described above.

EXAMPLE 17

4'-Dibromoacetyl-4'-demethylepipodophyllotoxin-β-D-2,3-di-O-dibromoacetyl-4,6-O-ethylideneglucoside (III) ($R_1$, $R_2$=—COCHBr$_2$)

(a) 4'-dibromoacetyl-4'-demethylepipodophyllotoxin (V) ($R_2$=—COCHBr$_2$)

5.0 g of 4'-demethylepipodophyllotoxin was dissolved in 150 ml of 1,2-dichloroethane. After adding 1.5 g of pyridine, the solution was cooled to $-5°$ to 10° C. To this solution, 3.8 g of dibromoacetyl chloride was added dropwise over a period of about 1.5 hours, and the mixture was further stirred for 0.5 hour. The reaction solution was washed with water, and the organic layer was dried over anhydrous magnesium sulfate and concentrated in vacuum to a volume of 50 ml to obtain a 1,2-dichloroethane solution of compound (V) ($R_2$=—COCHBr$_2$).

(b) 4,6-O-ethylidene-1-O-benzyloxycarbonyl-2,3-di-O-dibromoacetyl-β-D-glucopyranose (VIII) ($R_2$=—COCHBr$_2$)

5.1 g of 4,6-O-ethylidene-1-O-benzyloxycarbonyl-β-D-glucopyranose (VII) was suspended in 51 ml of 1,2-dichloroethane. After adding 3.6 g of pyridine, the suspension was cooled to 0° to 5° C. To this suspension, 7.8 g of dibromoacetyl chloride was added dropwise over a period of about one hour, and the mixture was further stirred for 30 minutes. Then, the reaction solution was washed with water, and the organic layer was dried over anhydrous magnesium sulfate and concentrated in vacuum to a volume of 25 ml to obtain a 1,2-dichloroethane solution of compound (VIII) ($R_1$=—COCHBr$_2$).

(c) 4,6-O-ethylidene-2,3-di-O-dibromoacetyl-β-D-glucopyranose (VI) ($R_1$=—COCHBr$_2$)

0.4 g of palladium black was added to 25 ml of the 1,2-dichloroethane solution of compound (VIII) ($R_1$=—COCHBr$_2$) of (b), and the solution was hydrogenated at $-10°$ to $-5°$ C. and an elevated pressure. After completion of the reaction, the catalyst was filtered off to obtain a 1,2-dichloroethane solution of compound (VI) ($R_1$=—COCHBr$_2$).

(d) 4'-dibromoacetyl-4'-demethylepipodophyllotoxin-β-D-2,3-di-O-dibromoacetyl-4,6-O-ethylideneglucoside (III) ($R_1$, $R_2$=—COCHBr$_2$)

25 ml of a 1,2-dichloroethane solution of compound (V) ($R_2$=—COCHBr$_2$) was combined with 50 ml of a 1,2-dichloroethane solution of compound (VI) ($R_1$=—COCHBr$_2$), and the combined solution was cooled to 10° C. 2.8 g of boron trifluoride ethyl etherate was added thereto dropwise over a period of about 1.5 hours. After completion of the addition, the reaction mixture was further stirred for 30 minutes. 2.0 g of pyridine was added thereto dropwise while the internal temperature was being kept at $-5°$ to 10° C., and the reaction mixture was washed with water. The organic layer was concentrated in vacuum, and the residue was recrystallized from methanol to obtain compound (III) ($R_1$, $R_2$=—COCHBr$_2$).

EXAMPLE 18

4'-Dichloroacetyl-4'-demethylepipodiphyllotoxin-β-D-2,3-di-O-trichloroacetyl-4,6-O-ethylideneglucoside (III) ($R_1$=—COCCl$_3$, $R_2$=—COCHCl$_2$)

(a) 4,6-O-ethylidene-1-O-benzyloxycarbonyl-2,3-di-O-trichloroacetyl-β-D-glucopyranose (VIII) ($R_1$=—COCCl$_3$)

25 ml of 1,2-dichloroethane solution of compound (VIII) ($R_1$=—COCCl$_3$) was obtained by the same reaction as in Example 17 except that dibromoacetyl chloride was replaced with trichloroacetyl chloride.

(b) 4,6-O-ethylidene-2,3-di-O-trichloroacetyl-β-D-glucopyranose (VI) ($R_1$=—COCCl$_3$)

25 ml of a 1,2-dichloroethane solution of compound (VI) ($R_1$=—COCCl$_3$) was obtained by the same reaction as in Example 17 (c) by using 25 ml of the solution obtained in (a).

(c) 4'-dichloroacetyl-4'-demethylepipodophyllotoxin-β-D-2,3-di-O-trichloroacetyl-4,6-O-ethylideneglucoside (III) ($R_1$=—COCCl$_3$, $R_2$=—COCHCl$_2$)

Compound (III) ($R_1$=—COCCl$_3$, $R_2$=—COCHCl$_2$) was obtained by reacting 25 ml of the solution obtained in (b) with 50 ml of a 1,2-dichloroethane solution containing compound (V) ($R_2$=—COCHCl$_2$) obtained in Example 16 (a) in the same manner as in Example 16 (d).

What is claimed is:

1. A process for producing etoposide represented by the formula (I):

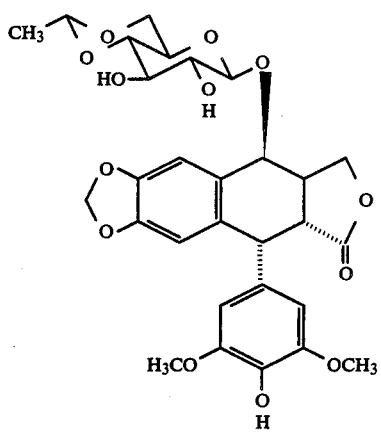

which comprises reacting a 4'-halogenoacetyl-4'-demethylepipodophyllotoxin-β-D-2,3-di-O-halogenoacetyl-4,6-O-ethylideneglucoside represented by the formula:

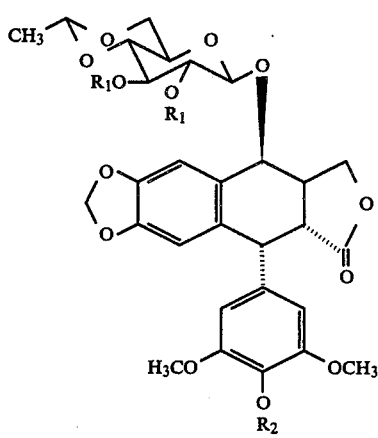

wherein $R_1$ and $R_2$, which may be the same or different, represent —COCHX$_2$ or —COCX$_3$, wherein X represents a chlorine atom, with lower $C_1$–$C_4$ alcohols having 1 to 3 hydroxyl groups in the presence of ammonium salt of an organic carboxylic acid to remove the halogenoacetyl groups at a temperature of −10° to 100° C.

2. A process according to claim 1, which comprises reacting a 4'-halogenoacetyl-4'-demethylepipodophyllotoxin-β-D-2,3-di-O-halogenoacetyl-4,6-O-ethylideneglucoside represented by the formula:

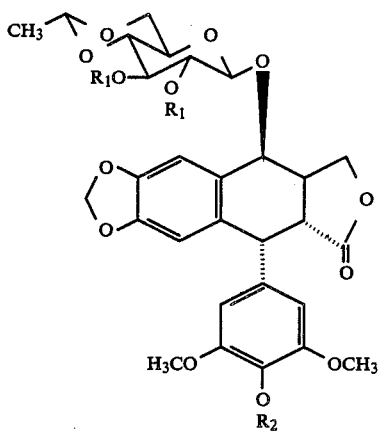

wherein $R_1$ and $R_2$, which may be the same or different, represent —COCHX$_2$ or —COCX$_3$, wherein X represents a halogen atom,
with at least an equivalent amount of methanol or ethanol to the compound of the formula (III) in the presence of ammonium acetate or ammonium formate in an amount of 5 to 100 w/w % based on the compound of the formula (III) to remove the halogenoacetyl groups at a temperature of −10° to 100° C.

3. A process according to claim 1, wherein said organic carboxylic acid salt is an ammonium salt of a $C_1$–$C_3$ saturated fatty acid.

4. A process according to claim 1, wherein said alcohol is methanol or ethanol.

5. A process according to claim 1, wherein at least one equivalent of said alcohol is used per equivalent of compound (III).

6. A process according to claim 1, wherein the amount of an ammonium salt of an organic carboxylic acid is 5 to 100 w/w %, based on the compound of the formula (III).

* * * * *